United States Patent
Browka et al.

(10) Patent No.: US 12,083,327 B2
(45) Date of Patent: Sep. 10, 2024

(54) SAFETY DEVICE WITH COLLAPSIBLE HOUSING AND TRIGGER ACTIVATION

(71) Applicant: Becton, Dickinson and Company, Franklin Lakes, NJ (US)

(72) Inventors: Edward P. Browka, Sherrill, NY (US); Laurie Sanders, Glen Ridge, NJ (US); Eli B. Nichols, Durham, NC (US); Philip C McNeill, Chappaqua, NY (US); Robert Henson, Fuquay Varina, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/129,128

(22) Filed: Mar. 31, 2023

(65) Prior Publication Data
US 2023/0293824 A1 Sep. 21, 2023

Related U.S. Application Data

(62) Division of application No. 17/007,071, filed on Aug. 31, 2020, now Pat. No. 11,642,471, which is a division of application No. 15/837,469, filed on Dec. 11, 2017, now Pat. No. 10,814,073.

(60) Provisional application No. 62/433,297, filed on Dec. 13, 2016.

(51) Int. Cl.
*A61M 5/32* (2006.01)

(52) U.S. Cl.
CPC ........ *A61M 5/3221* (2013.01); *A61M 5/3202* (2013.01); *A61M 5/3204* (2013.01); *A61M 5/321* (2013.01); *A61M 5/3232* (2013.01); *A61M 5/3243* (2013.01); *A61M 5/3273* (2013.01)

(58) Field of Classification Search
CPC .. A61M 5/3273; A61M 5/3202; A61M 5/321; A61M 5/3243; A61M 5/3204; A61M 5/3232; A61M 5/3221
See application file for complete search history.

(56) References Cited

U.S. PATENT DOCUMENTS

| | | |
|---|---|---|
| 4,795,432 A | 1/1989 | Karczmer |
| 4,804,371 A | 2/1989 | Vailancourt |
| 4,813,940 A | 3/1989 | Parry |
| 4,887,998 A * | 12/1989 | Martin ................... A61B 5/154 604/110 |
| 4,950,250 A | 8/1990 | Haber et al. |

(Continued)

FOREIGN PATENT DOCUMENTS

| | | |
|---|---|---|
| CA | 2803761 A1 | 12/2011 |
| CN | 103079610 A | 5/2013 |

(Continued)

OTHER PUBLICATIONS

"PCT International Search Report and Written Opinion in PCT/US2017/065679 dated Jun. 13, 2018, 15 pages".

(Continued)

*Primary Examiner* — Tasnim Mehjabin Ahmed
(74) *Attorney, Agent, or Firm* — Servilla Whitney LLC

(57) ABSTRACT

Drug delivery safety devices having trigger activation systems activated by pressure against the skin of a patient and which automatically shield the needle after withdrawing the needle from the skin of the patient.

11 Claims, 12 Drawing Sheets

(56) References Cited

U.S. PATENT DOCUMENTS

| | | | |
|---|---|---|---|
| 5,013,305 A * | 5/1991 | Opie | A61M 39/04 |
| | | | 604/263 |
| 5,395,347 A | 3/1995 | Blecher et al. | |
| 5,591,138 A | 1/1997 | Vaillancourt | |
| 5,688,241 A | 11/1997 | Asbaghi | |
| 5,984,899 A | 11/1999 | D'Alessio et al. | |
| RE36,885 E | 9/2000 | Blecher et al. | |
| 6,884,237 B2 | 4/2005 | Asbaghi | |
| 6,926,697 B2 | 8/2005 | Malenchek | |
| 7,347,838 B2 * | 3/2008 | Kulli | A61M 25/0618 |
| | | | 604/164.08 |
| 7,361,159 B2 | 4/2008 | Fiser et al. | |
| 7,513,888 B2 | 4/2009 | Sircom et al. | |
| 7,811,261 B2 | 10/2010 | Rubinstein et al. | |
| 7,922,698 B2 | 4/2011 | Riesenberger et al. | |
| 8,062,265 B2 | 11/2011 | Millerd | |
| 8,162,882 B2 | 4/2012 | Rubinstein et al. | |
| 8,303,541 B2 | 11/2012 | Chun | |
| 8,333,738 B2 | 12/2012 | Millerd | |
| 8,439,870 B2 | 5/2013 | Moyer et al. | |
| 8,496,627 B2 | 7/2013 | Chelak et al. | |
| 8,617,119 B2 | 12/2013 | Liversidge | |
| 8,636,688 B2 | 1/2014 | Shaw | |
| 8,636,703 B2 | 1/2014 | Foshee et al. | |
| 8,647,307 B2 | 2/2014 | Gratwohl et al. | |
| 8,663,129 B2 | 3/2014 | Allen et al. | |
| 8,747,355 B2 | 6/2014 | Rubinstein et al. | |
| 8,827,961 B2 | 9/2014 | Emmott et al. | |
| 8,968,241 B2 | 3/2015 | Liversidge | |
| 8,979,794 B2 | 3/2015 | Chevallier | |
| 9,050,416 B2 | 6/2015 | Feret et al. | |
| 9,061,106 B2 | 6/2015 | Roberts et al. | |
| 9,067,024 B2 | 6/2015 | Roberts et al. | |
| 9,186,466 B2 | 11/2015 | Zachek et al. | |
| 9,192,724 B2 | 11/2015 | Fourt et al. | |
| 9,352,099 B2 | 5/2016 | Roberts et al. | |
| 9,352,100 B2 | 5/2016 | Ward et al. | |
| 9,352,101 B2 | 5/2016 | Roberts et al. | |
| 9,370,327 B2 | 6/2016 | Teoh | |
| 9,408,632 B2 | 8/2016 | Erskine | |
| 9,445,760 B2 | 9/2016 | Allen et al. | |
| 9,694,140 B2 | 7/2017 | Rubinstein et al. | |
| 9,848,810 B2 | 12/2017 | Allen et al. | |
| 10,022,505 B2 | 7/2018 | Hu | |
| 10,814,073 B2 * | 10/2020 | Browka | A61M 5/3202 |
| 11,642,471 B2 * | 5/2023 | Browka | A61M 5/3204 |
| | | | 604/198 |
| 2003/0060774 A1 | 3/2003 | Woehr et al. | |
| 2003/0181867 A1 | 9/2003 | Bressler et al. | |
| 2004/0010227 A1 | 1/2004 | Riesenberger et al. | |
| 2008/0221528 A1 | 9/2008 | Lanz | |
| 2009/0299295 A1 | 12/2009 | Rubinstein et al. | |
| 2010/0298770 A1 | 11/2010 | Rubinstein et al. | |
| 2011/0288491 A1 | 11/2011 | Newman et al. | |
| 2014/0135706 A1 | 5/2014 | Rubinstein et al. | |
| 2014/0228772 A1 | 8/2014 | Ward et al. | |
| 2014/0364803 A1 | 12/2014 | Rubinstein et al. | |
| 2015/0094659 A1 | 4/2015 | Schraga | |
| 2015/0182704 A1 | 7/2015 | Chevallier | |
| 2015/0190580 A1 | 7/2015 | Imai et al. | |
| 2015/0190586 A1 | 7/2015 | Takemoto | |
| 2016/0095983 A1 | 4/2016 | Lewkonya et al. | |
| 2018/0161523 A1 | 6/2018 | Sanders et al. | |

FOREIGN PATENT DOCUMENTS

| | | |
|---|---|---|
| EP | 0750915 A2 | 1/1997 |
| EP | 2585146 B1 | 3/2017 |
| JP | 2007519474 A | 7/2007 |
| JP | 2013529973 A | 7/2013 |
| JP | 2014079375 A | 5/2014 |
| MX | 2013000081 | 3/2013 |
| MX | 349289 B | 7/2017 |
| WO | 2009114777 A1 | 9/2009 |
| WO | 2012000833 A1 | 1/2012 |
| WO | 2012013587 A1 | 2/2012 |
| WO | 2013138549 A1 | 9/2013 |

OTHER PUBLICATIONS

"PCT Invitation to Pay Additional Fees, and, Where Applicable, Protest Fee in PCT/US2017/065718 dated Apr. 9, 2018, 13 pages".

* cited by examiner

SAFETY DEVICE WITH COLLAPSIBLE HOUSING AND TRIGGER ACTIVATION

CROSS-REFERENCE TO RELATED APPLICATIONS

This application is a divisional of U.S. patent application Ser. No. 17/007,071, filed on Aug. 31, 2020, now allowed, which is a divisional of U.S. patent application Ser. No. 15/837,469, filed on Dec. 11, 2017, issued as U.S. Pat. No. 10,814,073 on Oct. 27, 2020, which claims priority under 35 U.S.C. § 119(e) to U.S. Provisional Application No. 62/433,297, filed Dec. 13, 2016, the disclosure of which is incorporated herein by reference in its entirety.

TECHNICAL FIELD

The present disclosure relates generally to a drug delivery safety device having a passive trigger activation system, i.e., structure for activation of the trigger which is engaged upon use of the drug delivery device to provide post-injection needle shielding without additional intervention by the user.

BACKGROUND

Accidental needle sticks with a used needle can transmit disease. As a result, most prior art needle assemblies have a needle shield. Some prior art needle shields define a rigid sleeve that is manually telescoped or rotated over a needle cannula after use. This procedure often requires the healthcare worker to hold the syringe barrel in one hand and the shield in the other. Because some medical procedures require the application of pressure to the penetration site after the needle has been removed, healthcare workers are often unable to use both hands for shielding the needle cannula. In these situations, workers will deposit the used medical implement on a nearby surface with the intention of shielding the used needle at a more convenient time. However, until the needle is shielded or properly disposed of, it presents a potential danger to other people.

As a further risk to healthcare workers, the additional post-injection activity required to manually shield a used needle, regardless of whether the procedure requires one hand or both hands, increases the likelihood of an accidental needle stick. There is therefore a need for needle shielding systems and devices which are triggered automatically upon use of the needle to treat a patient, thus avoiding any need for the healthcare worker to take extra steps or further handle the medical device to achieve safe shielding of the used needle. Such automatic shielding devices and mechanisms are often referred to as passive medical safety devices or passive shielding systems. In particular, there is a need for passive needle safety devices which require lower force to trigger the shielding mechanism.

SUMMARY

A first aspect pertains to a drug delivery safety device comprising a body attached to a needle hub. The body encloses a rotating cam engaged in a slot through a sidewall of the body. The slot comprises three segments: a proximal angled lead ramp, a ledge at the distal end of the angled lead ramp for seating the rotating cam, and an axial slot portion distal to the ledge. The needle hub includes a needle cannula which is surrounded by a flexible housing. The flexible housing connects the body to a lock clip near the distal end of the needle cannula such that the needle cannula is substantially covered by the flexible housing but the distal tip of the cannula is exposed. The passive shielding system is activated by a trigger mechanism comprising a first spring which connects the rotating cam to the lock clip and a second spring in the body extending from the rotating cam proximally toward the needle hub. The first spring biases the lock clip distally and the second spring biases the rotating cam distally. The force applied to the rotating cam by the second spring is sufficient to seat the rotating cam on the ledge of the slot and to maintain its seated position prior to use of the cannula for injection.

In one or more embodiments, the first spring may surround the needle cannula within the flexible housing.

In one or more embodiments, the lock clip may be housed in a cap which is attached to the flexible housing, the cap including an aperture to permit the cannula to pass therethrough.

When the drug delivery safety device is attached to a syringe and used for injection, a proximally-directed force greater than the distally-directed force of the second spring is applied to the lock clip. Thus, the first spring is compressed, and the flexible housing retracts proximally. The proximal force also moves the lock clip proximally along the shaft of the cannula. This proximal force is typically applied when the exposed tip of the needle cannula is inserted into the skin of a patient to the desired depth for administering an injection. The proximal force overcomes the biasing force of the second spring to move the rotating cam in a proximal direction, off of the ledge and down the angled lead ramp. The angled surface of the angled lead ramp causes the rotating cam to rotate as it moves to the proximal end of the angled lead ramp. When the proximal force is subsequently decreased (as when the needle cannula is removed from the patient's skin after completion of the injection) the first spring decompresses, allowing the second spring to again apply sufficient distal force to the rotated rotating cam to move it distally along the axial slot portion. This force moves the lock clip in a distal direction past the distal tip of the needle cannula to cover the distal tip.

In one or more embodiments, the needle hub of the drug delivery safety device may be attached to the barrel of a syringe.

In one or more embodiments, the flexible housing may be a spring coil, a butterfly spring, a zig-zag coil or a rolled-sheet coil. In one or more embodiments, the flexible housing may have slack when in the pre-injection extended position that permits further extension of the flexible housing post-injection to permit the lock clip to cover the distal tip of the needle cannula.

In one or more embodiments, instead of two independent springs, the first and second springs may be composed of a single spring that is fed through the rotating cam.

In one or more embodiments, there are at least two slots in the body. In one or more embodiments, there are two slots in the body on opposite sides of the body.

In one or more embodiments, the lock clip may be a hook clip which contacts the shaft of the needle cannula near the distal end and slides proximally along its length as the needle cannula is inserted into the patient's skin and the first spring is compressed. During the passive shielding portion of the procedure (after removal of the needle cannula from the patient's skin), the hook clip moves distally along the needle cannula and past the distal tip so that the hook portion of the hook clip covers the distal tip.

In one or more embodiments, the lock clip may be comprised of two pieces, one on each side of the needle cannula and each having a contact point with the needle cannula surface. This lock clip functions in the passive drug delivery safety device as discussed above with respect to the hook clip, except that when the two-piece clip moves distally past the distal tip of the needle cannula, the two pieces close together to cover the distal tip.

In one or more embodiments, the drug delivery safety device may further comprise a removable sleeve which fits over the body to prevent triggering of the trigger mechanism. This feature allows the device to be used to fill a syringe prior to injection without activating the passive shielding system. The removable sleeve is removed after filling of the syringe so that the passive shielding system becomes available for triggering when used to administer an injection. In one embodiment, the anti-triggering sleeve fits over the body and includes an interior surface having a protrusion (e.g., a ridge) which engages the axial slot portion of the slot, thereby preventing movement and rotation of the rotating cam.

The anti-triggering system may further comprise a cap which is a removable fill cap covering the exposed tip of the needle cannula. Prior to filling, both the anti-triggering cap and the fill cap may be present on the device. To fill a syringe, the fill cap is removed. Because of the presence of the anti-triggering sleeve, a syringe can be filled multiple times without triggering the passive safety mechanism. If it is desired to transport the filled syringe or delay injection, the fill cap can optionally be re-attached. When it is desired to administer an injection, the anti-triggering sleeve is removed (with the fill cap, if present) to permit movement and rotation of the rotating cam.

A second aspect pertains to a drug delivery safety device comprising a trigger mechanism connecting a needle hub to a lock clip near the distal end of the needle cannula. A flexible housing surrounds the needle cannula and connects the needle hub to the lock clip such that the needle cannula is substantially covered by the flexible housing but the distal tip of the cannula is exposed. The passive shielding system is activated by a trigger mechanism comprising a spring which connects the needle hub to the lock clip. The device also includes a body which engages the needle hub. The body has an inner cavity with proximal and distal ends, and a Y-clip disposed in the inner cavity. First and second arms of the Y-clip are held open by engagement with first and second pockets at the distal end of the inner cavity as well as by distal force exerted by the spring which biases the first and second arms toward the "splayed" or "open" position. The first and second arms of the Y-clip have angled surfaces so that when they are moved toward each other (inwardly or toward a "closed" position) an axial vector force is created. In one or more embodiments the Y-clip may include at least two protrusions which function as travel stops to prevent the Y-clip from leaving the body, thus setting the distance of distal travel of the lock clip.

In one or more embodiments, the spring may surround the needle cannula within the flexible housing.

In one or more embodiments, the lock clip may be housed in a cap which is attached to the flexible housing, the cap including an aperture to permit the cannula to pass therethrough.

When the drug delivery safety device is used to administer an injection, a proximally-directed force applied to the lock clip compresses the spring distally. Compression of the spring retracts the flexible housing in a proximal direction and also moves the lock clip proximally along the needle cannula to expose more of the distal end of the needle cannula. This proximal force is typically applied when the exposed tip of the needle cannula is inserted into the skin of a patient to the desired depth for administering an injection. The proximal force of the compressed spring creates slack in the flexible housing, which allows the Y-clip to move proximally within the body to release the first and second arms from the first and second pockets of the body, and allows the first and second arms to move inwardly toward each other, creating an axial vector force. When the proximal force is subsequently decreased (as when the needle cannula is removed from the patient's skin after completion of the injection) the spring decompresses, and the axial vector force moves the lock clip distally past the distal tip of the needle cannula to cover the distal tip.

In one or more embodiments, the needle hub of the drug delivery safety device may be attached to the barrel of a syringe.

In one or more embodiments, the flexible housing may be a spring coil, a butterfly spring, a zig-zag coil or a rolled-sheet coil. In one or more embodiments, the flexible housing may have slack when in the pre-injection extended position that permits further extension of the flexible housing post-injection to permit the lock clip to cover the distal tip of the needle cannula.

In one or more embodiments, the lock clip may be a hook clip which contacts the needle cannula near the distal end and slides proximally along its length as the needle cannula is inserted into the patient's skin, compressing the spring. During the passive shielding portion of the procedure (after removal of the needle cannula from the patient's skin), the hook clip moves distally along the needle cannula and past the distal tip so that the hook covers the distal tip.

In one or more embodiments, the lock clip may be comprised of two pieces, one on each side of the needle cannula and each having a contact point with the shaft of the needle cannula. This lock clip functions in the passive drug delivery safety device as discussed above with respect to the hook clip, except that when the two-piece clip moves distally past the distal tip of the needle cannula, the two pieces close together to cover the distal tip.

In one or more embodiments, the drug delivery safety device may further comprise a removable anti-triggering cap which fits over the body and prevents triggering of the trigger mechanism. This feature allows the device to be used to fill a syringe prior to injection without activating the passive shielding system. The removable anti-triggering cap is removed after filling of the syringe so that the passive shielding system becomes available for triggering when used to administer an injection. In one embodiment the cap may have an outer wall which fits over the exterior wall of the body and an interior wall which is positioned between the first and second legs of the Y-clip when the cap is placed over the body. The position of the interior wall between the first and second arms keeps the arms "splayed" or "open" even when the spring is compressed, thus preventing release of the first and second arms from the first and second pockets when proximal force is applied.

The anti-triggering system may further comprise a second cap which is a removable fill cap covering the exposed tip of the needle cannula. Prior to filling, both the anti-triggering cap and the fill cap are present on the device. To fill a syringe, the fill cap is removed. Because of the presence of the anti-triggering cap, the syringe can be filled multiple times without triggering the passive safety mechanism. If it is desired to transport the filled syringe or delay injection, the fill cap can optionally be re-attached. When it is desired to administer an injection, the anti-triggering cap is removed (with the fill cap, if present) to permit movement of the arms of the Y-clip.

A third aspect pertains to a drug delivery safety device comprising a needle hub with a needle cannula, and at least two flexible arms axially adjacent to the needle cannula connecting a trigger housing near the distal end of the cannula to the needle hub. The trigger housing includes an aperture in the distal wall which permits the needle cannula to pass therethrough. A trigger mechanism inside the trigger housing is comprised of a spring connecting the trigger housing to the flexible arms, and a double leaf spring lock clip. The lock clip is positioned near the distal end of the needle cannula, such that the tip of the needle cannula is exposed through an aperture in the lock clip. A first leaf of the lock clip removably engages the flexible arms and a second leaf of the lock clip engages the trigger housing. The second leaf of the lock clip includes a distal needle tip cover which, prior to triggering, is in contact with the needle cannula near its distal end, thus keeping the needle tip cover out of alignment with the apertures of the trigger housing and the lock clip. Prior to use for administering an injection, the spring biases the trigger housing and the lock clip in the distal direction, preventing proximal movement of the trigger housing and the lock clip along the shaft of the needle cannula, and maintaining engagement of the first leaf of the lock clip with the flexible arms.

In one or more embodiments, the needle hub of the drug delivery safety device may be attached to the barrel of a syringe by attachment of the needle hub to the collar of the syringe barrel.

In one or more embodiments, the spring may be a spring coil or a leaf spring.

In one or more embodiments, the trigger housing may be configured to fit over an end-cap connecting the at least two flexible arms. The end-cap includes an aperture aligned with the apertures of the trigger housing and the lock clip, permitting the needle cannula to pass therethrough. In one or more embodiments, the end-cap may be integrally molded with the at least two flexible arms.

In one or more embodiments, the spring may surround the end-cap and, prior to use, be biased against the distal interior wall of the trigger housing, thereby forcing the trigger housing and lock clip distally to maintain engagement of the first leaf of the lock clip with the at least two flexible arms.

In one or more embodiments, the first leaf of the lock clip may removably engage the at least two arms by removable engagement with the end-cap, e.g., by means of a proximal hook on the first leaf which engages a shelf on the end-cap.

When the drug delivery safety device is used to administer an injection, a distally-directed force applied to the trigger housing compresses the spring, moving the trigger housing and the lock clip proximally toward the at least two flexible arms. This movement allows the first leaf of the lock clip to disengage from the end-cap. Tension released from the first leaf of the lock clip allows it to flex to an unloaded state, thus maintaining the disengaged position during continued proximal movement of the trigger housing. After disengagement, the needle can be inserted to the desired depth with the at least two flexible arms flexing outward. Upon removal of the needle cannula from the skin, post-injection, the spring fully decompresses and the trigger housing moves distally along the shaft of the needle cannula past the distal tip. At this point the needle tip cap of the second leaf of the lock clip is released from contact with the needle cannula and flexes into the needle tip covering position. Typically, the force required to move the trigger housing and release the first leaf of the lock clip is less than the force to flex the two or more flexible arms so that the passive shielding mechanism is triggered within a short distance during injection In one or more embodiments, the drug safety delivery device may further comprise structure for preventing triggering of the passive safety mechanism prior to administering the injection. This feature allows the device to be used to fill a syringe prior to injection without activating the passive shielding system. The anti-triggering structure is removed or disabled after filling of the syringe so that the passive shielding system becomes available for triggering during injection. In one or more embodiments, the anti-triggering structure may comprise a removable cap or sleeve which includes a rib to hold the first leaf of the lock clip in the engaged position and constrain proximal motion of the trigger housing during fill. Subsequent to filling the syringe, the cap is removed to allow proximal movement of the trigger housing and passive shielding upon injection. In certain embodiments, the anti-triggering component includes a removable fill cap which covers the needle cannula exposed at the distal end of the removable cap or sleeve prior to filling the syringe.

In an alternative embodiment, the anti-triggering component may comprise a bracket and pull-pin. The bracket (e.g., a "U" bracket) engages the drug delivery safety device in either side of the trigger housing to constrain movement of the trigger housing during the syringe filling process. The pull-pin facilitates removal of the bracket by pulling it to the side. This permits proximal movement of the trigger housing and passive shielding upon injection. This embodiment may also comprise a removable fill cap to cover the exposed needle cannula prior to filling the syringe. The fill cap may include a slot to accommodate fitting over the side pull-pin.

The user first removes the fill cap to fill the syringe which, due to the anti-triggering constraints of the removable sleeve or cap, can be done multiple times. When the user desires to administer an injection, the second component of the anti-triggering mechanism (e.g., sleeve/cap or bracket/pull pin) is removed from the drug delivery safety device to permit triggering of the passive safety feature during the injection. If the user intends to delay using the filled syringe for administering an injection, the fill cap can be re-applied until such time as injection is desired. In this case, the fill cap and second component are both removed prior to injection to allow triggering.

In any of these three aspects, it is to be understood that the needle tip may be exposed through the distal end of the housing of the locking mechanism or the housing may cover the needle tip provided that the needle tip is exposed through the distal end of the lock clip.

BRIEF DESCRIPTION OF THE DRAWINGS

FIG. 11A shows details of the trigger housing prior to injection, FIG. 11B shows details of the trigger housing upon triggering of the passive safety mechanism during injection, and FIG. 11C shows details of the trigger housing in needle-protecting locked position post-injection.

DETAILED DESCRIPTION

As used herein, the term "proximal," "proximally-directed" and related terms with respect to the drug safety delivery device refer to a direction toward the needle hub or toward the syringe when the drug safety delivery device is attached to a syringe.

As used herein the term "distal, "distally-directed" and related terms with respect to the drug safety delivery device refer to a direction toward the needle tip or toward the patient's skin when the device is in use for administering an injection.

Before describing several exemplary embodiments, it is to be understood that the disclosure not limited to the details of construction or process steps set forth in the following description. The disclosure is capable of other embodiments and of being practiced or being carried out in various ways.

In general, provided are safety devices for passive shielding the distal tip of a needle cannula after it is used for injection. The safety devices include a collapsible or flexible structure directly or indirectly connecting the needle hub to a locking clip positioned at the distal end of the needle cannula. Initially, prior to use, the needle tip is exposed through the locking clip. The collapsible or flexible structure is longitudinally oriented between the needle hub and the locking clip, and surrounds, or runs adjacent to, the cannula. Prior to use of the safety device there is stored energy in the form of tension on the safety device which prevents the safety device from triggering and keeps the needle tip exposed for use. When the needle tip is inserted into the skin of the patient, the stored energy in the system is released and the safety device is activated or triggered. However, once activation occurs, the safety device does not shield the needle as long as the needle remains in the skin. This permits the user to continue to insert the needle to the desired depth. Only upon removal of the needle from the skin does the activated safety device automatically advance the locking clip forward to cover the tip of the needle, thereby automatically and passively preventing needle stick injury as soon as the injection is completed. In certain embodiments, the safety devices include additional components which allow for filling of a syringe, without triggering the passive safety mechanism, prior to injection.

These features can be achieved by several embodiments of the safety device. In addition to the advantages of automatic and immediate shielding of the used needle, these several embodiments provide the advantage of requiring less force against the patient's skin during injection to trigger the passive safety mechanism. The various aspects and embodiments also provide a passive mechanism for shielding a needle which activates during injection over a shorter stroke distance.

The Rotating Force Trigger

Figure 1:
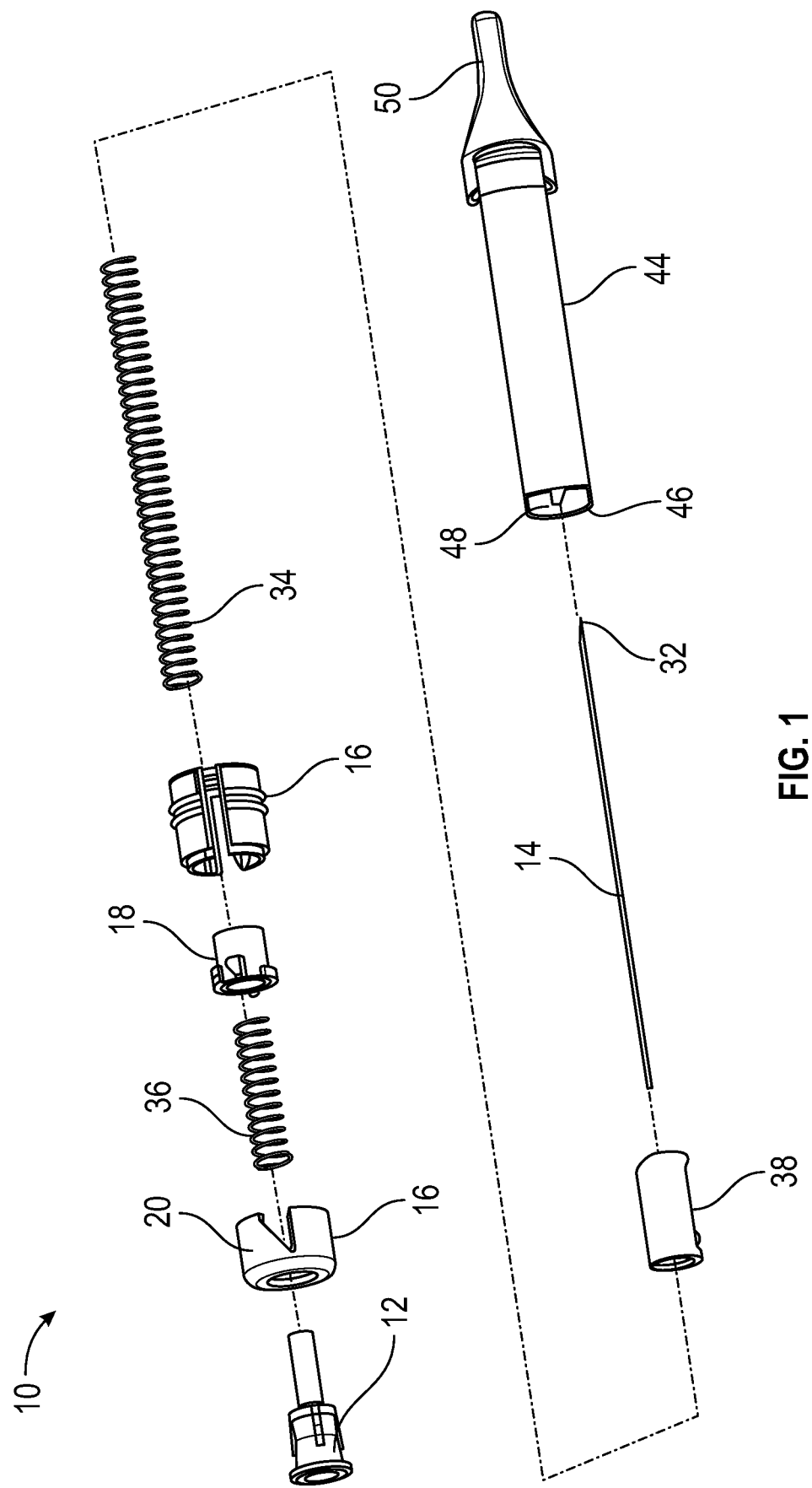
FIG. 1 shows one embodiment of the drug safety delivery device.
Figure 2:
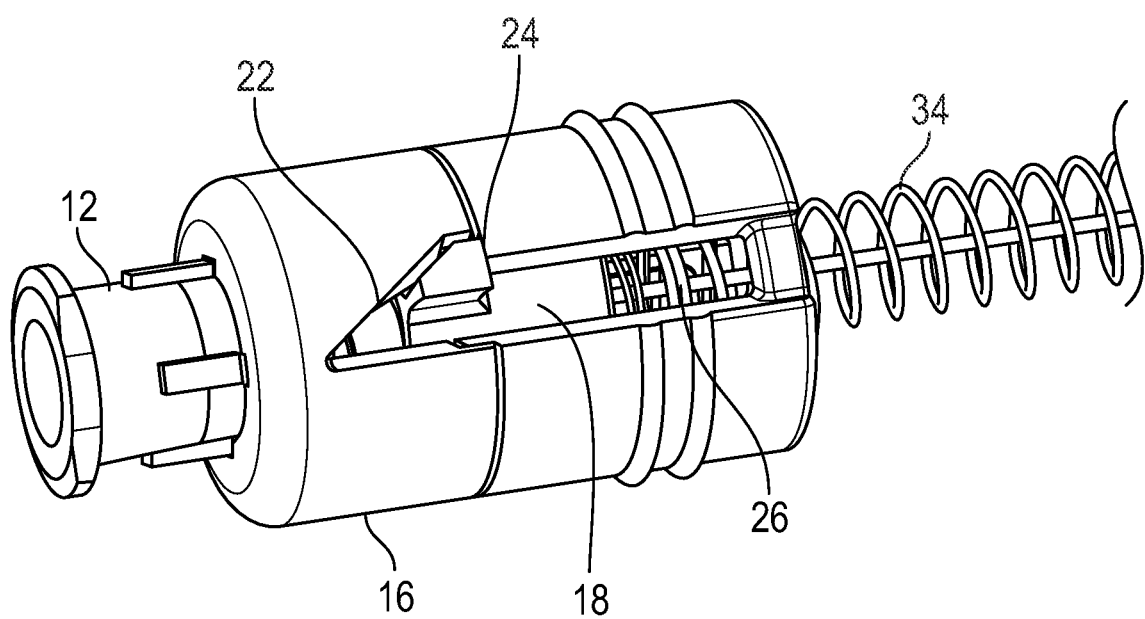
FIG. 2 shows one embodiment of a body and rotating cam assembly of the drug safety delivery device.

One embodiment, shown generally in FIG. 1, is referred to herein as the "rotating force trigger." The rotating force trigger drug delivery safety device 10 comprises a needle hub 12 for attachment of drug delivery safety device 10 to a syringe, needle hub 12 having an attached needle cannula 14. A body 16, which engages needle hub 12, encloses a rotating cam 18. Rotating cam 18 engages body 16 through a slot in a sidewall 20 of body 16. As shown in more detail in FIG. 2, the slot comprises three segments: a proximal angled lead ramp 22, a ledge 24 at the distal end of the angled lead ramp for seating the rotating cam, and an axial slot portion 26 distal to the ledge.

Figure 3:
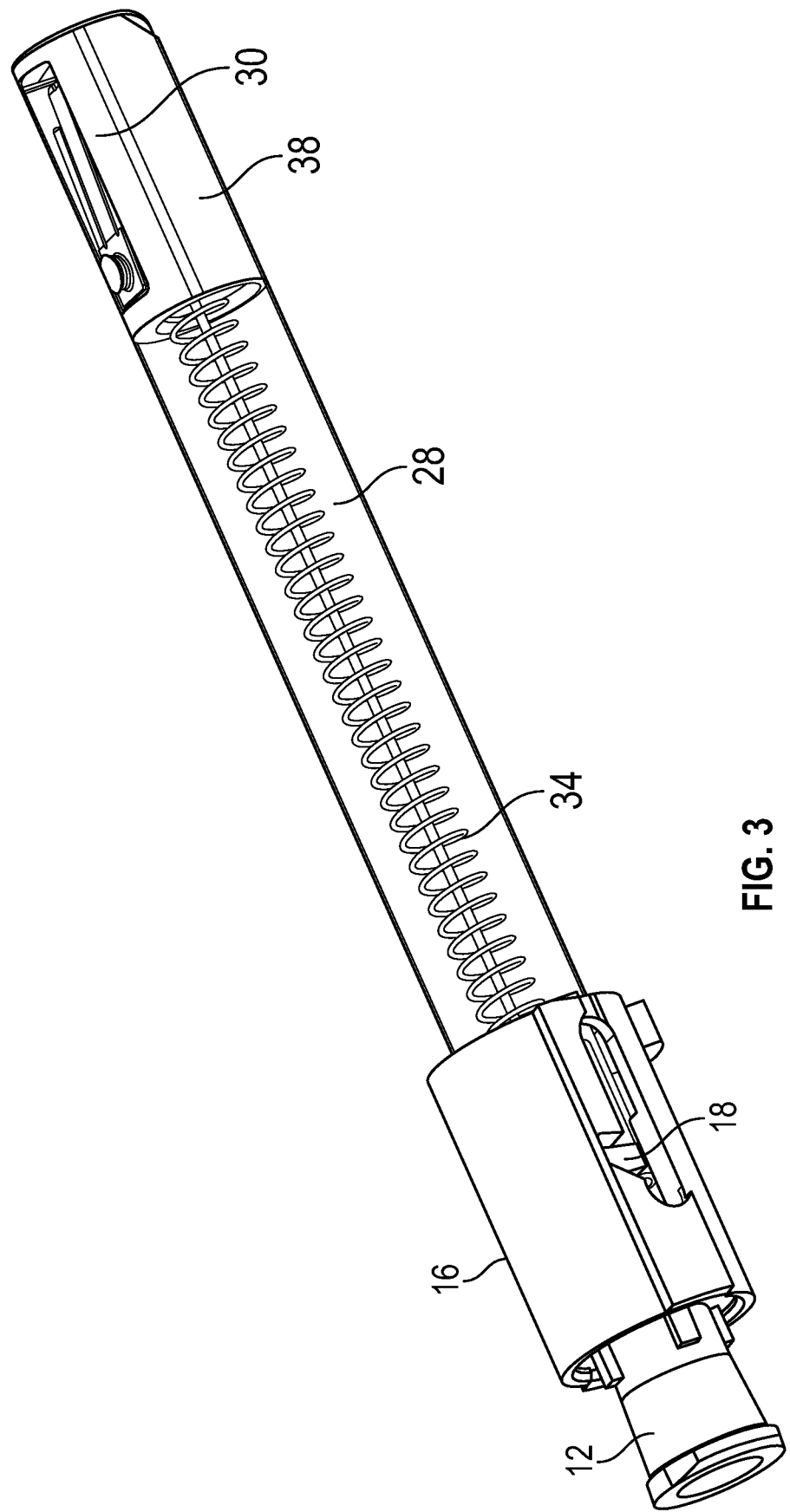
FIG. 3 shows one embodiment of the drug safety delivery device.

As illustrated in FIG. 3, needle cannula 14 is surrounded by a flexible housing 28 which connects rotating cam 18 to a lock clip 30 near the distal end of needle cannula 14 such that needle cannula 14 is substantially covered by the flexible housing but distal tip 32 of the cannula is exposed. The passive shielding system includes a trigger mechanism comprising a first spring 34 which connects rotating cam 18 to lock clip 30 and a second spring 36 in body 16 extending from rotating cam 18 proximally toward needle hub 12. First spring 34 biases lock clip 30 distally and second spring 36 biases rotating cam 18 distally. Lock clip 30 may be housed in a cap 38 which is attached to flexible housing 28.

Figure 4:
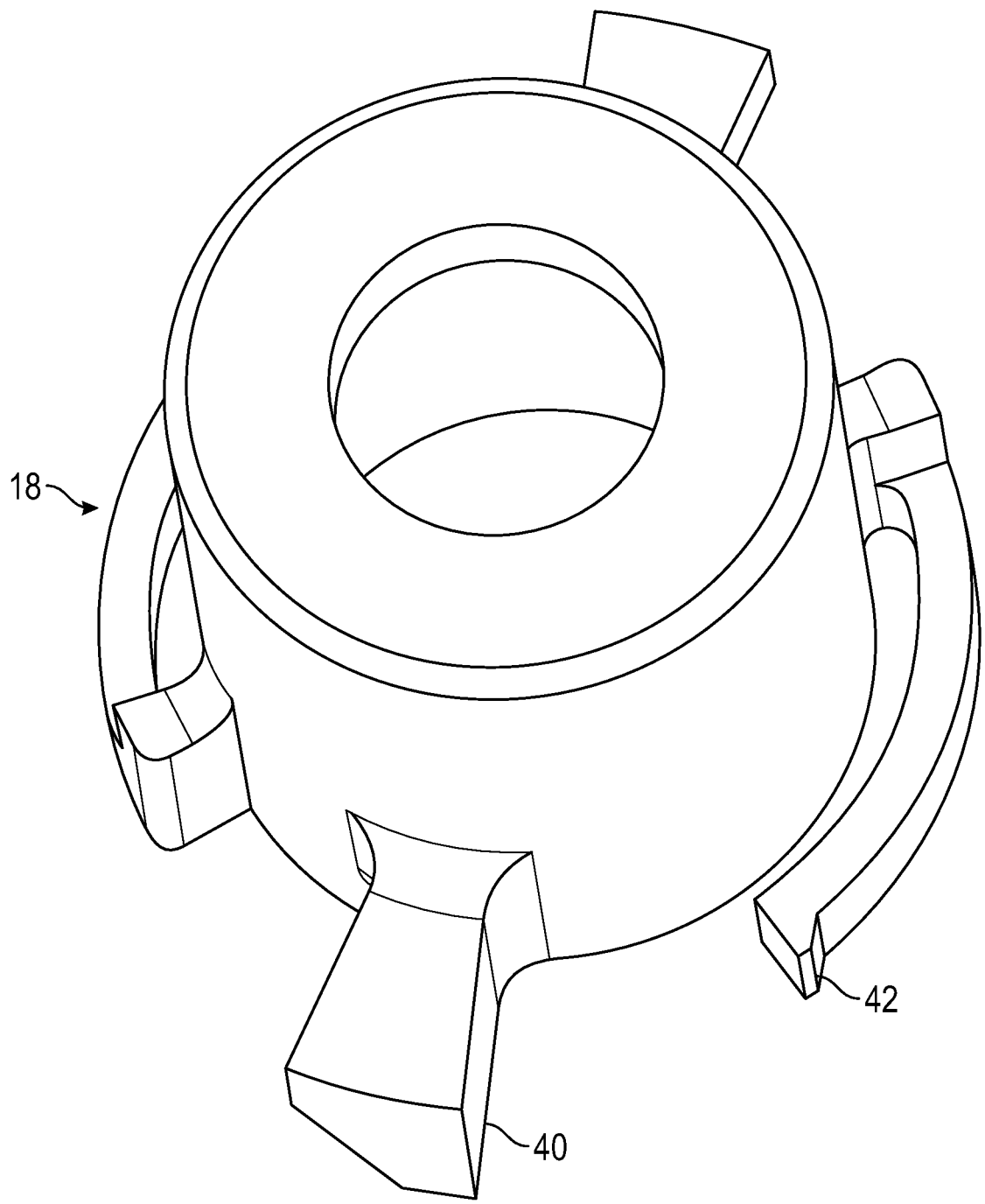
FIG. 4 shows one embodiment of a rotating cam.

An embodiment of rotating cam 18, configured for engagement with two slots opposite each other in body 16, is illustrated in more detail in FIG. 4. Tabs 40 are configured to engage the slots in body 16. Wings 42 may be present on the periphery of rotating cam 18 for engagement with threads or channels on the interior wall of body 16 to facilitate smooth rotation in only one direction. Wings 42 start in an un-flexed state and, as rotating cam 18 rotates, wings 42 may ride over ribs on the inner surface of housing 16. The ribs and head of wings 42 have biased ramps such that a ratchet is created. This prevents tabs 40 from reengaging with ledge 24 of body 16 during distal travel. Tabs 40 may be cylindrical to allow for a line contact area with angled lead ramp 22 or they may have a matching helix to increase the contact area, reducing binding and resistance to motion.

An anti-triggering component useable with the drug delivery safety device is also shown in FIG. 1. The anti-triggering component is a removable anti-triggering sleeve 44 which is hollow and configured to fit over drug safety delivery device 10 to engage body 16. An interior surface 46 of anti-triggering sleeve 44 includes a rib 48 configured to engage axial slot portion 26 and prevent rotation of rotating cam 18 when sleeve 44 is in place. Removable fill cap 50 covers the distal opening of anti-triggering sleeve 44 to prevent access to needle cannula 14 until the syringe is to be filled, at which time it is removed and rib 48 of sleeve 44 engaged in axial slot portion 26 prevents rotation of rotating cam 18 during fill. When the syringe is filled and an injection is to be administered, removable anti-triggering sleeve 44 is removed from drug delivery safety device 10. This anti-triggering configuration also allows for a very low force trigger at time of use, because the anti-trigger rib prevents triggering during shipping and shelf storage.

The Linear Distance Trigger

Figure 5:
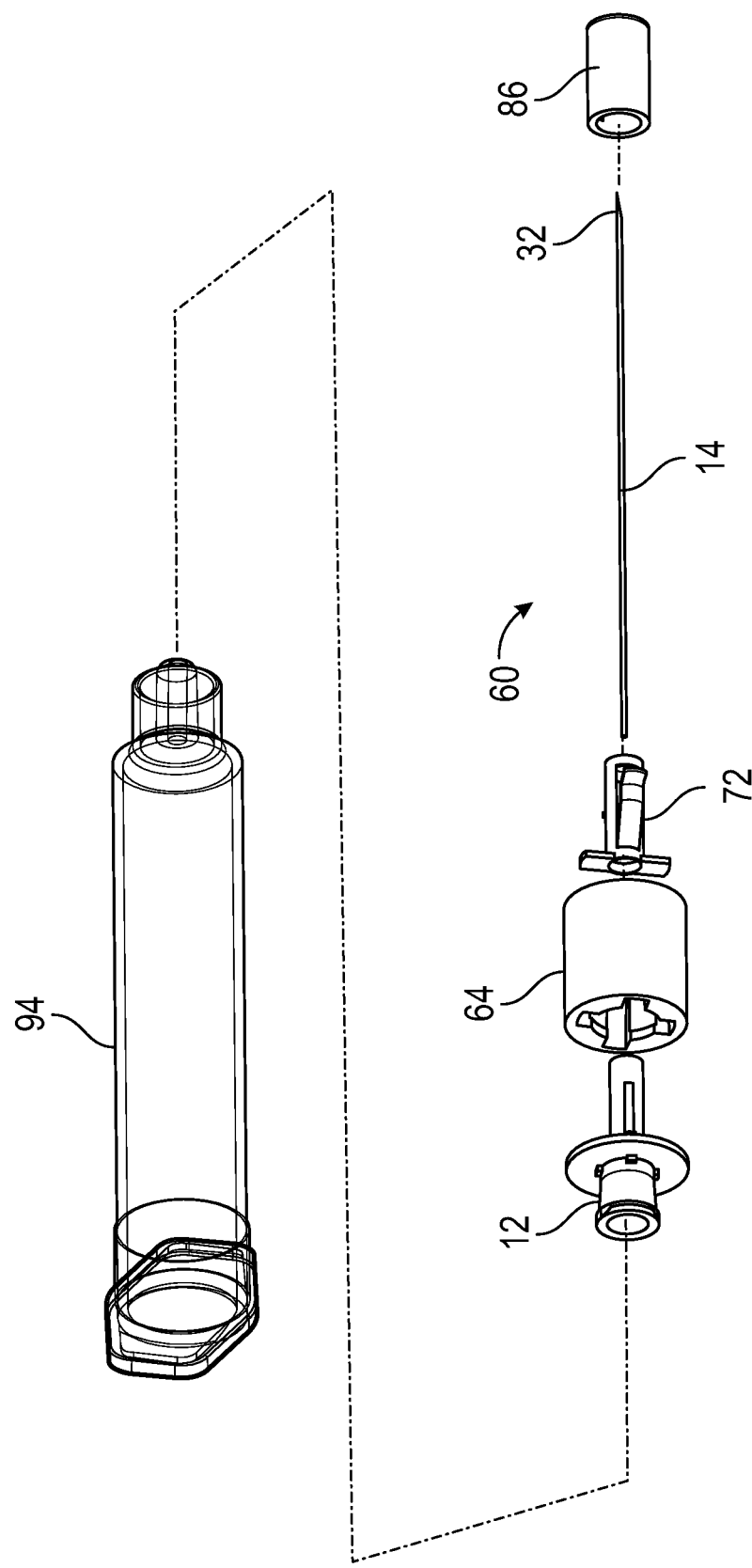
FIG. 5 shows a second embodiment of a drug safety delivery device.
Figure 6:
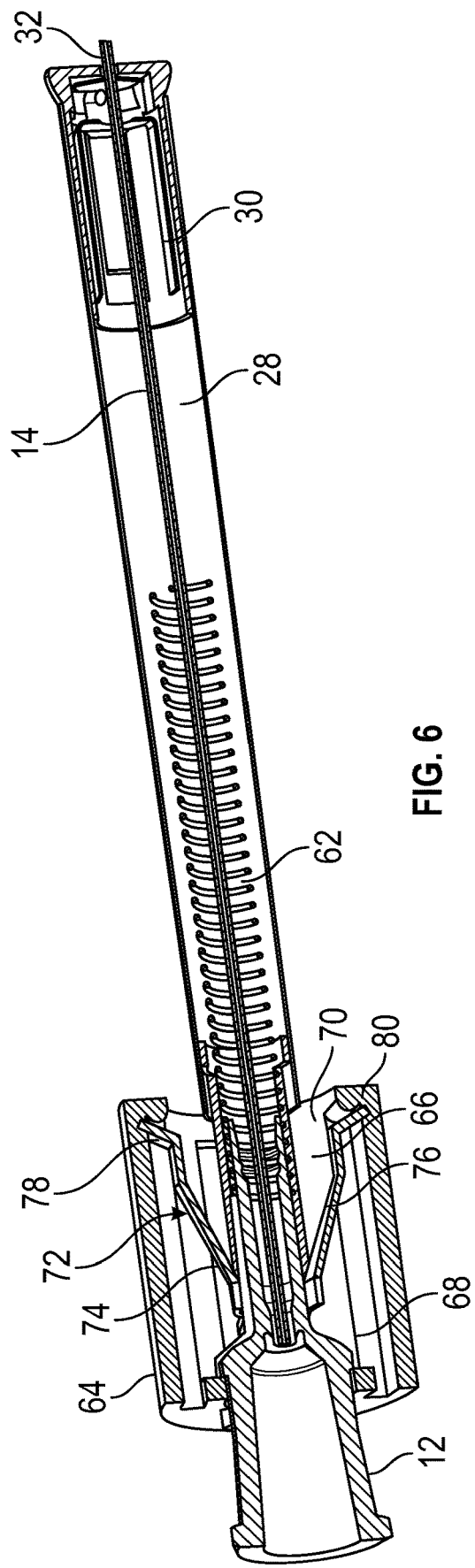
FIG. 6 shows a second embodiment of a drug safety delivery device.

One embodiment, shown generally in FIGS. 5 and 6, is referred to herein as the "linear distance trigger." This drug delivery safety device 60 comprises a spring 62 connecting a needle hub 12 to a lock clip 30 near the distal end of the needle cannula 14. Needle hub 12 provides attachment of drug delivery safety device 60 to a syringe 94. A flexible housing 28 surrounds needle cannula 14 and connects Y-clip 72 to lock clip 30 such that needle cannula 14 is substantially covered by flexible housing 28 but the distal tip 32 of cannula 14 is exposed.

A body 64 fittingly engages needle hub 12. Body 64 has an inner cavity 66 with proximal end 68 and distal end 70, and a Y-clip 72 disposed in inner cavity 66. First arm 74 and second arms 76 of Y-clip 72 are held open by engagement, respectively, with first pocket 78 and second pocket 80 at the distal end of the inner cavity and by force of spring 62 which biases the first and second arms toward the "splayed" or "open" position. First and second arms 74, 76 of Y-clip 72 have angled surfaces 73, as shown in more detail in FIG. 7. Lock clip 30 is housed in a cap 86 which is attached to flexible housing 28.

Figure 7:
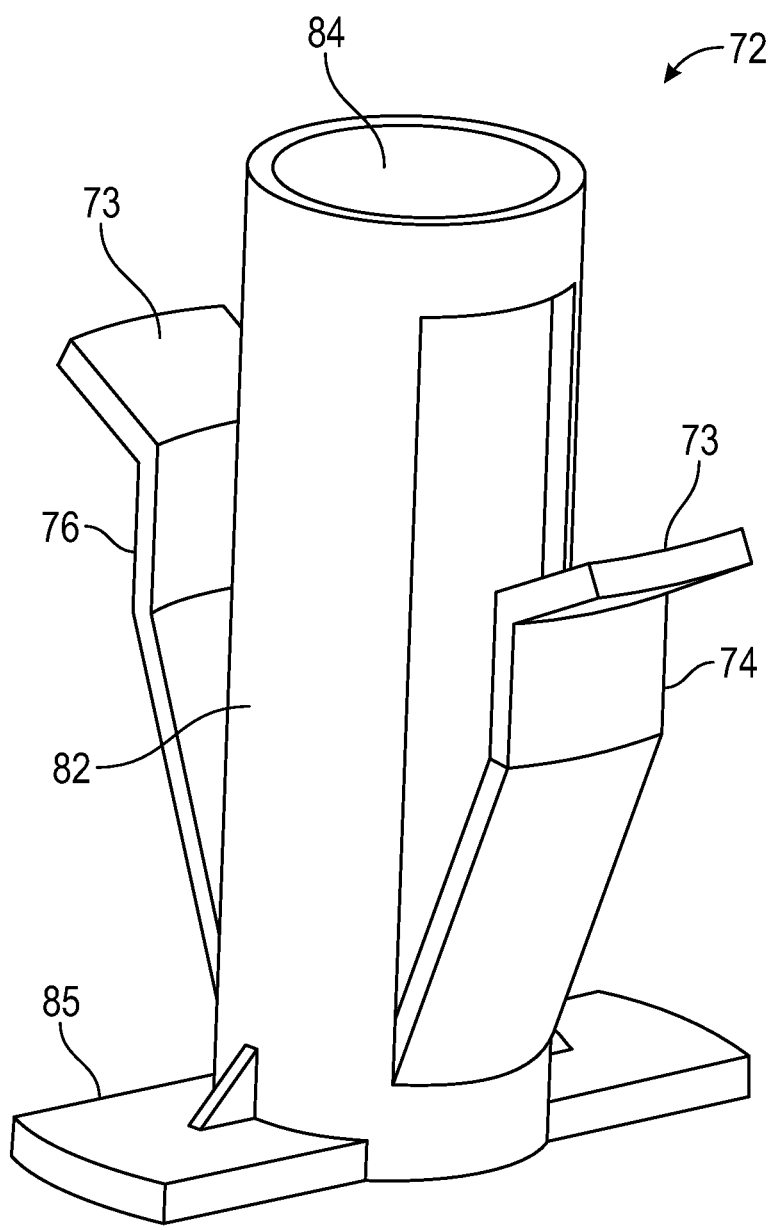
FIG. 7 shows one embodiment of a Y-clip of the drug safety delivery device.

Y-clip 72 is shown in more detail in FIG. 7, including a sleeve 82 which fittingly engages needle hub 12 and includes aperture 84 which permits needle cannula 14 to pass therethrough. Travel stop 85 is a protruding member that engages with a lip on the inside of body 64 to limit distal travel of the Y-clip.

Figure 8:
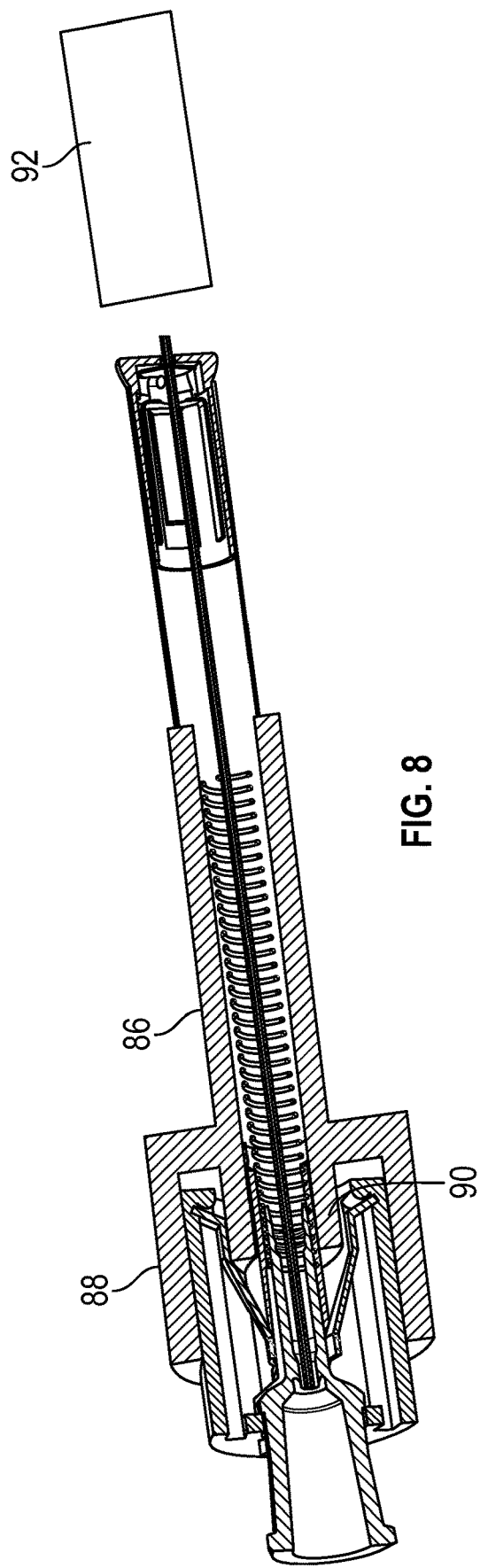
FIG. 8 shows one embodiment of an anti-triggering device for use with the drug safety delivery device.

FIG. 8 illustrates an anti-triggering component for use with. drug delivery safety device 60. Removable anti-triggering cap 86 comprises an outer wall 88 configured to fit over the outside of body 64. Anti-triggering cap 86 further comprises an interior wall 90 which sits between first and second arms 74, 76 of Y-clip 72 when anti-triggering cap 86 is in place. Interior wall 90 thus prevents release of first and second arms 74, 76 from first and second pockets 78, 80. Removable fill cap 92 covers the distal end of drug delivery safety device 60 to prevent access to needle cannula 14 until syringe 94 is to be filled, at which time it is removed and Y-clip 72 prevents movement of first and second arms 74, 76 during fill. When syringe 94 is filled and an injection is to be administered, anti-triggering cap 86 is removed from drug delivery safety device 60.

Front-End Trigger

Figure 9:
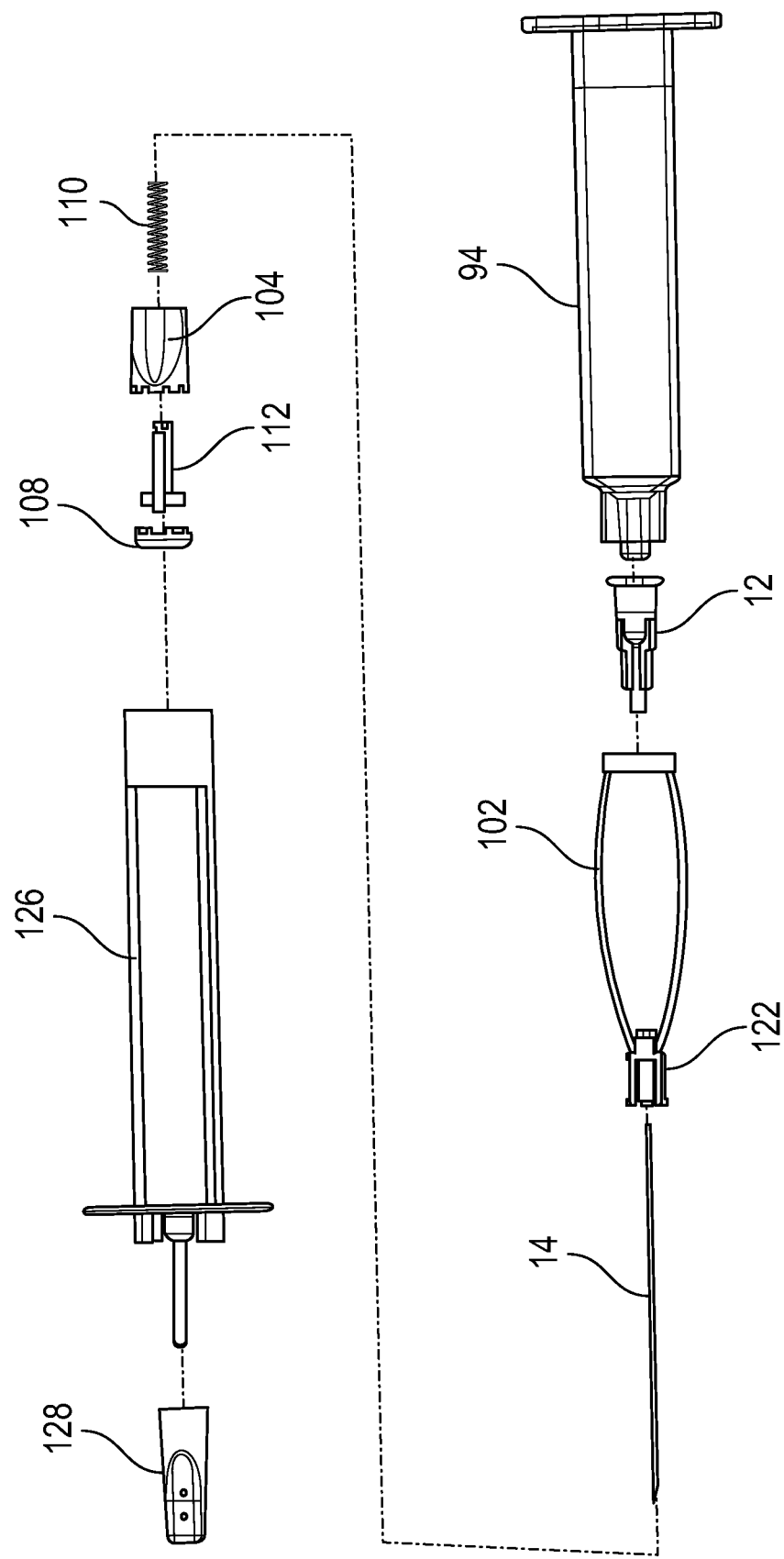
FIG. 9 shows a third embodiment of a drug safety delivery device.
Figure 10:
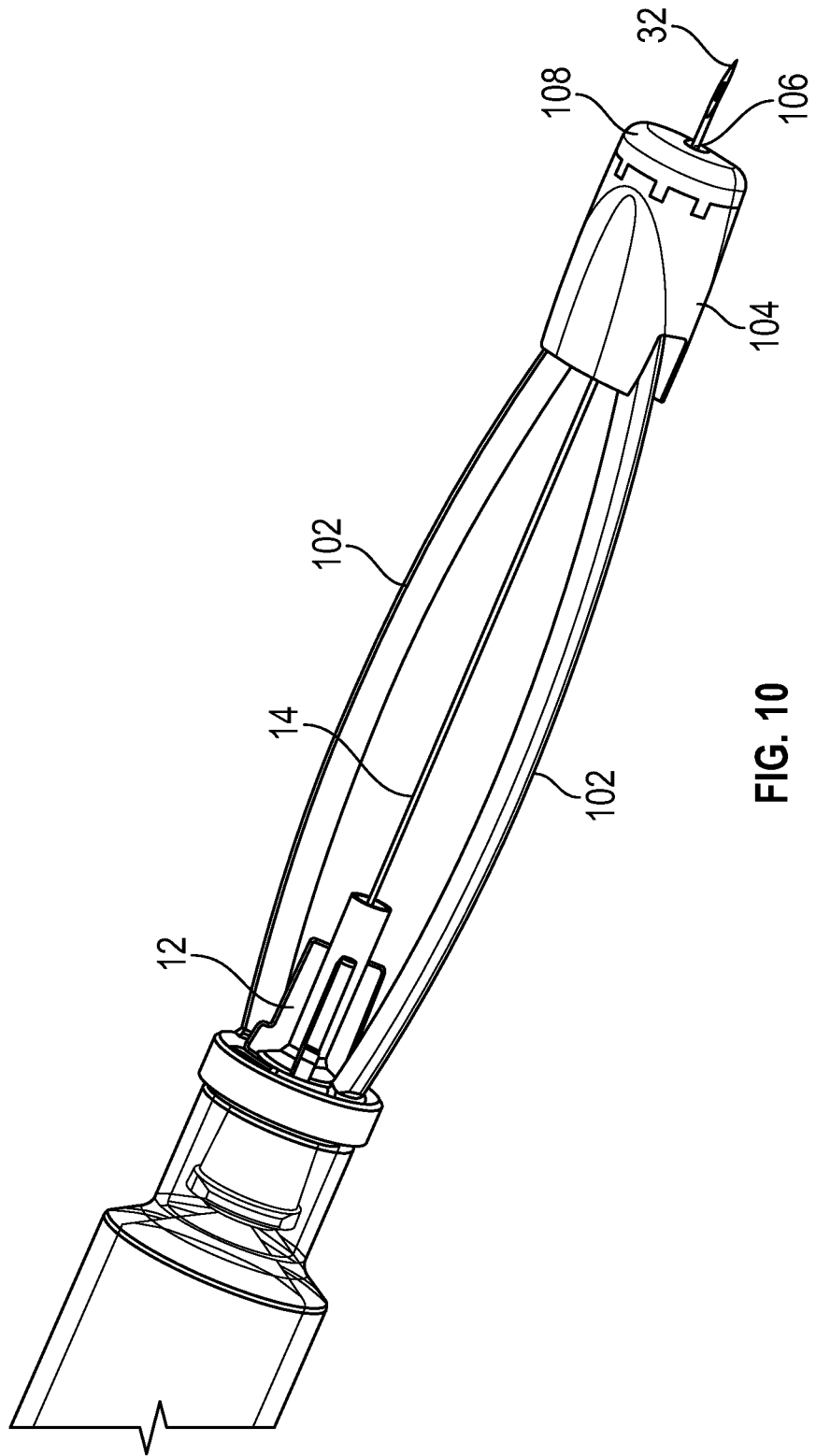
FIG. 10 shows a third embodiment of a drug safety delivery device.
Figure 11A:
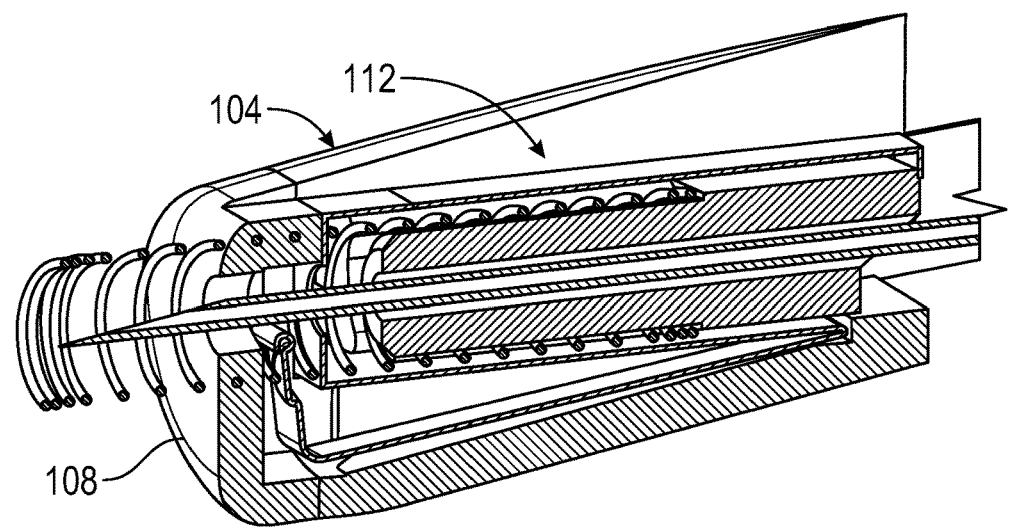
FIG. 11A-C shows one embodiment of a trigger housing usable with the drug safety delivery device.

One embodiment, shown generally in FIG. 9, is referred to as the "front-end trigger." This drug delivery safety device 100 comprises a needle hub 12 with a needle cannula 14 for attachment to a syringe 94, and at least two flexible arms 102 axially adjacent to needle cannula 14 to connect a trigger housing 104 to needle hub 12. As shown in FIGS. 10 and 11, trigger housing 104 includes an aperture 106 in a distal wall 108 thereof, through which distal tip 32 of cannula 14 is exposed. A trigger mechanism inside trigger housing 104 is comprised of a spring 110 (shown in FIG. 11) connecting trigger housing 104 to flexible arms 102. The trigger mechanism also includes a double leaf spring lock clip 112, shown in detail in FIG. 12, having a first leaf 114 which removably engages flexible arms 102 and a second leaf 116 which engages trigger housing 104 to retain lock clip 112 within trigger housing 104. Second leaf 116 includes a distal needle tip cover 118 which, prior to triggering (FIG. 11A), is in contact with the needle cannula to keep needle tip cover 118 out of alignment with aperture 106 of trigger housing 104 and aperture 120 of lock clip 112.

Figure 11B:
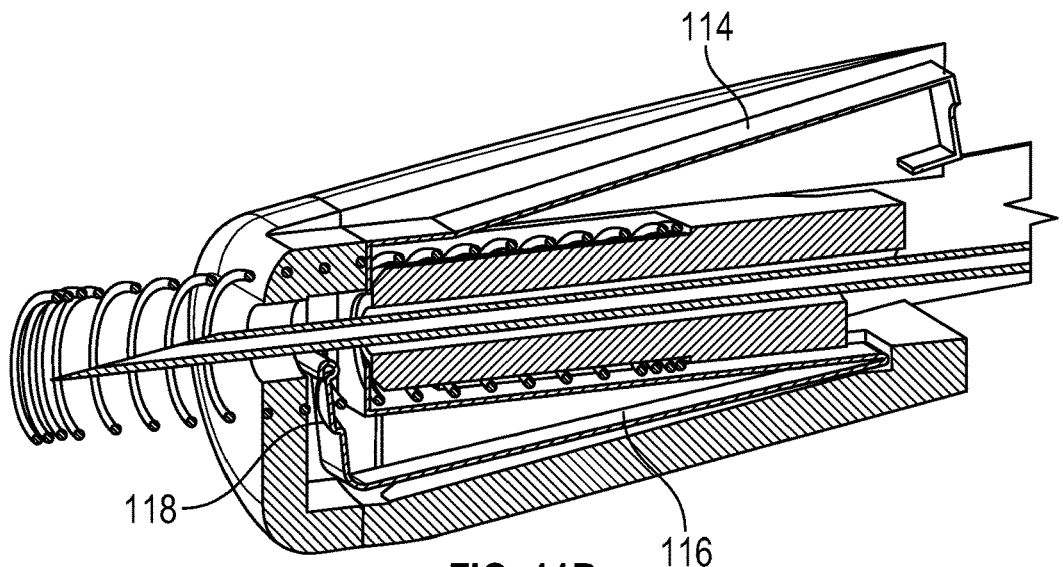
Figure 11C:
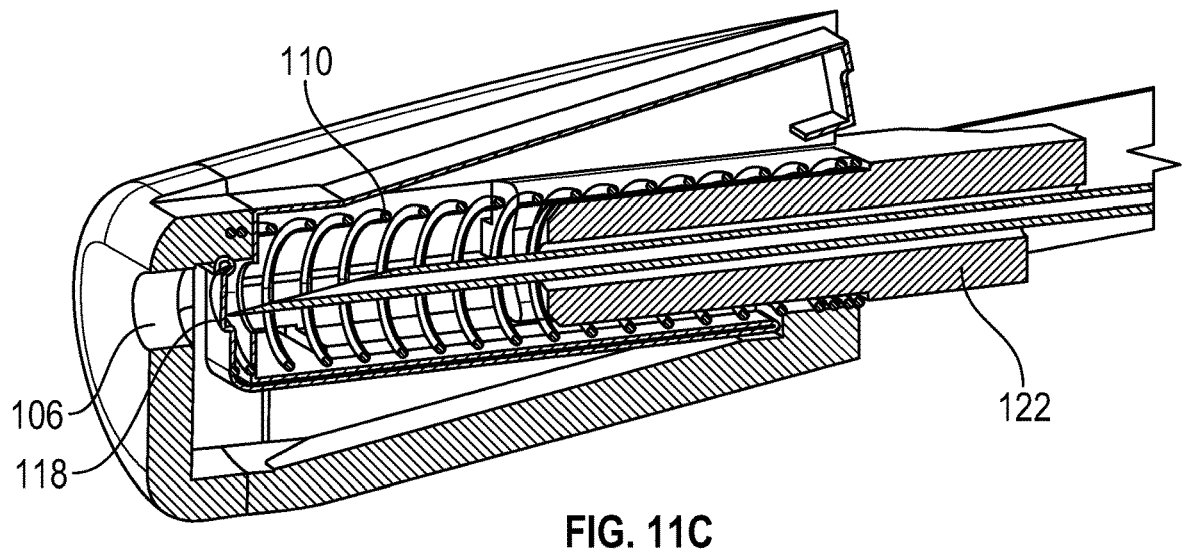
Figure 12:
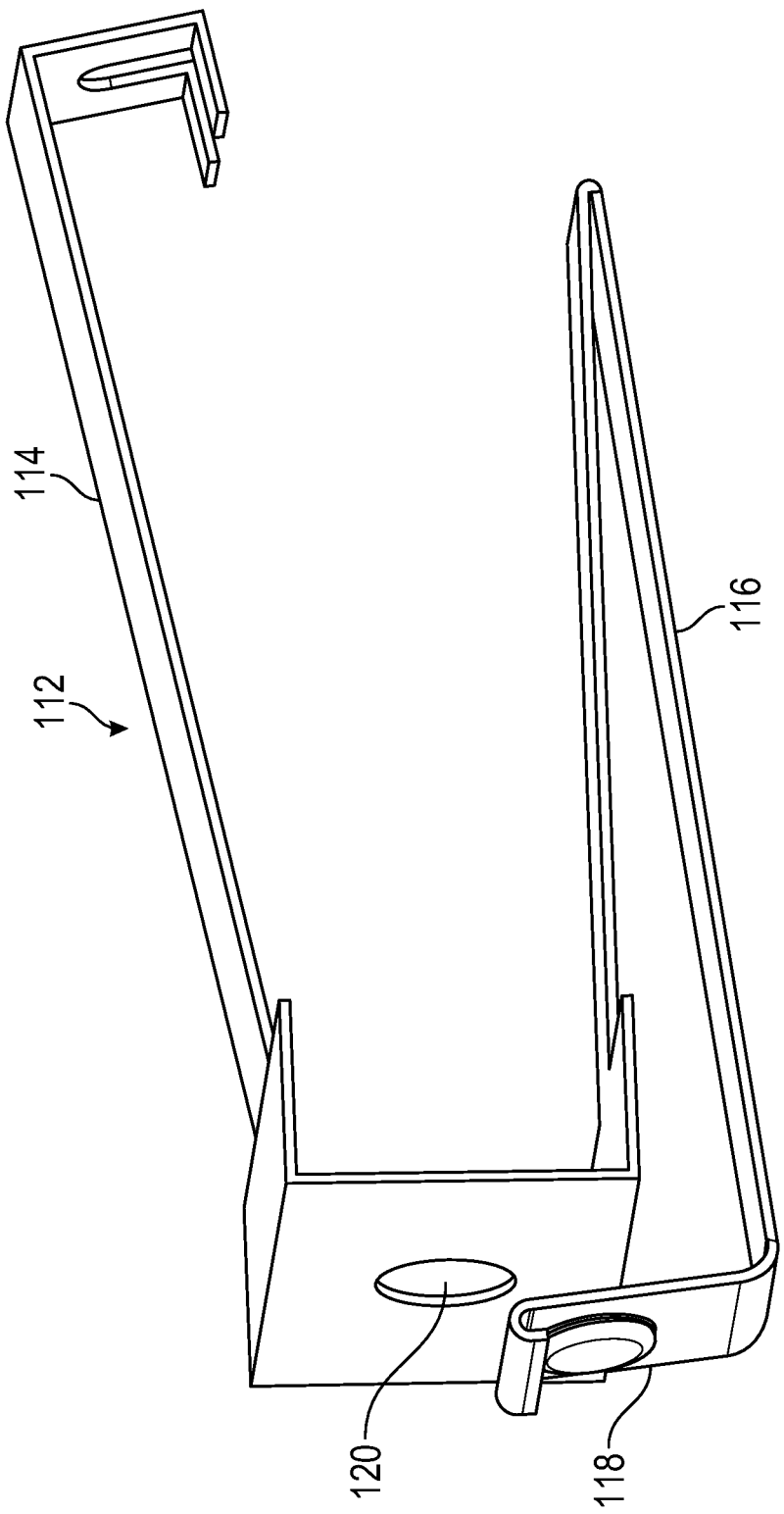
FIG. 12. shows one embodiment of a double leaf spring lock clip.

An end-cap 122 connects the distal ends of the two flexible arms. Trigger housing 104 fits over end-cap 122. As shown in FIGS. 11A-C, spring 110 indirectly connects lock clip 112 to flexible arms 102 via engagement with end-cap 122. The end-cap includes an aperture 124 aligned with aperture 106 of trigger housing 104 and aperture 120 of lock clip 112.

FIG. 9 also shows an anti-triggering component for use with drug delivery safety device 100. Removable anti-triggering sleeve 126 is hollow and configured to fit over drug safety delivery device 100 to engage needle hub 12. Anti-triggering sleeve 126 includes a rib configured to hold down first leaf 114 of lock clip 112. Removable anti-triggering sleeve 126 constrains motion of trigger housing 104 when in place. Removable fill cap 128 covers the distal opening of anti-triggering sleeve 126 to prevent access to needle cannula 14 until the syringe is to be filled, at which time it is removed and the rib of anti-triggering sleeve 126 prevents disengagement of first leaf 114 from flexible arms 102. When syringe 94 is filled and an injection is to be administered, removable sleeve 126 is removed from drug delivery safety device 100.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A drug delivery safety device comprising:
   a needle hub including a cannula having a distal tip;
   a trigger mechanism comprising a spring connecting the needle hub to a lock clip at a distal end of the needle cannula
   a flexible housing surrounding the needle cannula and connecting a Y-clip to the lock clip such that the distal tip of the cannula is exposed;
   a body configured to engage the hub, the body including an exterior wall, an inner cavity having a proximal end and a distal end, and the Y-clip disposed within the cavity, the Y-clip including first and second arms having angled surfaces, wherein the first and second arms are held open by engagement with first and second pockets at the distal end of the inner cavity and by distal force exerted by the spring;
   wherein a proximally-directed force applied to the lock clip compresses the spring and releases tension on the flexible housing, whereby the first and second arms of the Y-clip are released from the first and second pockets and the Y-clip moves proximally; and
   wherein a subsequent decrease in the proximal force applied to the lock clip decompresses the spring and moves the lock clip in a distal direction such that the lock clip covers the distal tip of the cannula.

2. The drug delivery safety device of claim 1, wherein the lock clip is housed in a cap which is attached to the flexible housing, the cap including an aperture to permit the cannula to pass therethrough.

3. The drug delivery safety device of claim 2, wherein the flexible housing is selected from the group consisting of a spring coil, a butterfly spring, a zig-zag coil, a rolled-sheet coil, a film tube, a filament, and telescoped sleeves.

4. The drug delivery safety device of claim 2, wherein the flexible housing is slack when the drug delivery safety device is in a pre-injection configuration.

5. The drug delivery safety device of claim 1, wherein the lock clip is a hook clip or a two-piece clip.

6. The drug delivery safety device of claim 1 which is attached to a syringe via the needle hub.

7. The drug delivery safety device of claim 1, further comprising a removable anti-triggering cap which fits over the body and prevents triggering of the trigger mechanism, the cap comprising:

an outer wall which fits over the exterior wall of the body; and an interior wall which engages the first and second arms of the Y-clip when the cap is fitted over the exterior wall of the body, thereby preventing release of the first and second arms from the first and second pockets when proximal force is applied.

8. The drug delivery safety device of claim 7, further comprising a fill cap covering the exposed distal tip of the cannula.

9. The drug delivery safety device of claim 1, further comprising a lip on the body.

10. The drug delivery safety device of claim 1, further comprising a travel stop.

11. The drug delivery safety device of claim 10, wherein the travel stop is a protruding member configured to engage with the lip on the body.

* * * * *